US012281350B2

(12) United States Patent
Addy et al.

(10) Patent No.: US 12,281,350 B2
(45) Date of Patent: *Apr. 22, 2025

(54) PROCESSES AND SYSTEMS FOR CATALYTIC MANUFACTURE OF WAX ESTER DERIVATIVES

(71) Applicant: CARGILL, INCORPORATED, Wayzata, MN (US)

(72) Inventors: Jeff Addy, Chandler, AZ (US); James H. Brown, Chandler, AZ (US); Clay Daly, Chandler, AZ (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/159,735

(22) Filed: Jan. 26, 2023

(65) Prior Publication Data

US 2023/0227867 A1    Jul. 20, 2023

Related U.S. Application Data

(63) Continuation of application No. 17/456,166, filed on Nov. 23, 2021, which is a continuation of application No. 14/578,075, filed on Dec. 19, 2014, now Pat. No. 11,248,245.

(51) Int. Cl.
| | |
|---|---|
| *C12P 7/6436* | (2022.01) |
| *C11C 3/00* | (2006.01) |
| *C11C 3/10* | (2006.01) |
| *C12N 9/20* | (2006.01) |
| *C12P 7/6458* | (2022.01) |

(52) U.S. Cl.
CPC ............ *C12P 7/6436* (2013.01); *C11C 3/003* (2013.01); *C11C 3/10* (2013.01)

(58) Field of Classification Search
None
See application file for complete search history.

(56) References Cited

U.S. PATENT DOCUMENTS

| | | | |
|---|---|---|---|
| 4,329,298 A | 5/1982 | Brown et al. | |
| 4,360,387 A | 11/1982 | Brown et al. | |
| 4,826,767 A | 5/1989 | Hansen | |
| 5,968,530 A | 10/1999 | Arquette | |
| 6,123,979 A | 9/2000 | Hepburn et al. | |
| 6,280,746 B1 | 8/2001 | Arquette et al. | |
| 6,559,182 B1 | 5/2003 | Purcell | |
| RE38,141 E | 6/2003 | Brown et al. | |
| 6,692,762 B2 | 2/2004 | Cain et al. | |
| 7,695,727 B2 | 4/2010 | Magee et al. | |
| 8,349,594 B2 | 1/2013 | Pearce et al. | |
| 8,545,702 B1 | 10/2013 | Shah et al. | |
| 8,742,148 B1 | 6/2014 | Liu et al. | |
| 10,435,726 B2 * | 10/2019 | Addy ..................... | C11C 3/003 |
| 11,248,245 B2 * | 2/2022 | Addy ..................... | C11C 3/003 |
| 11,757,544 B2 | 9/2023 | Wendt et al. | |
| 11,767,543 B2 | 9/2023 | Addy et al. | |
| 11,767,544 B2 | 9/2023 | Addy et al. | |
| 11,773,418 B2 | 10/2023 | Addy et al. | |
| 12,180,530 B2 | 12/2024 | Addy et al. | |
| 12,203,122 B2 | 1/2025 | Addy et al. | |
| 2003/0054509 A1 | 3/2003 | Lee et al. | |
| 2004/0208904 A1 | 10/2004 | Touitou et al. | |
| 2005/0014237 A1 | 1/2005 | Lee | |
| 2005/0176597 A1 | 8/2005 | Kodali et al. | |
| 2007/0113467 A1 | 5/2007 | Abou-Nemeh | |
| 2007/0190186 A1 | 8/2007 | Loh et al. | |
| 2010/0136065 A1 | 6/2010 | Schlossman et al. | |
| 2010/0330629 A1 | 12/2010 | Basheer et al. | |
| 2013/0052701 A1 | 2/2013 | Basheer et al. | |
| 2013/0149414 A1 | 6/2013 | Favre et al. | |
| 2013/0183259 A1 | 7/2013 | Kleiman et al. | |
| 2013/0185991 A1 | 7/2013 | Nishiama et al. | |
| 2013/0253211 A1 | 9/2013 | Allan | |
| 2014/0017741 A1 | 1/2014 | Nielsen et al. | |
| 2014/0120589 A1 | 5/2014 | Austic et al. | |
| 2014/0303389 A1 | 10/2014 | Crosby et al. | |
| 2016/0177349 A1 * | 6/2016 | Addy ..................... | C11C 3/003 435/134 |
| 2016/0177350 A1 * | 6/2016 | Addy ..................... | C12P 7/6436 435/134 |
| 2022/0073957 A1 | 3/2022 | Addy et al. | |

(Continued)

FOREIGN PATENT DOCUMENTS

| | | |
|---|---|---|
| JP | H06-022690 A | 2/1994 |
| JP | H07-079786 A | 3/1995 |
| JP | 2001-520175 T | 10/2001 |

(Continued)

OTHER PUBLICATIONS

Avery Sengupta et al., "Comparative Study of Sterol Ester Synthesis using Termomyces Lanuginosus Lipase in Stirred Tank and Packed-Bed Bioreactors," J. Am Oil Chem Soc, vol. 87, p. 1019-1025 (2010).

Jose A. Arcos et al., "Continuous Enzymatic Esterification of Glycerol with (Poly)Unsaturated Fatty Acids in a Packed-Bed Reactor," Biotechnology and Bioengineering, vol. 68, No. 5, p. 563-570 (Jun. 5, 2000).

Aran H-Kittikun et al., "Continuous production of monoacylglycerols from palm olein in packed-bed reactor with immobilized lipase PS," Biochemical Engineering Journal 40, p. 116-120 (2008).

Anders Falk Vikbjerg et al., "Continuous Production of Structured Phospholipids in a Packed Bed Reactor with Lipase from Thermomyces lanuginosa," AOCS, Vo. 82, No. 4 (2005).

(Continued)

*Primary Examiner* — David Steadman

(57) ABSTRACT

Processes for transesterifying wax esters. Implementations may include: providing a feedstock including wax esters, contacting the feedstock with a lipase, and catalytically transesterifying the wax esters in the feedstock with the lipase to form a transesterified product. An oxidative stability index (OSI) of the transesterified product may be greater than an OSI of the feedstock.

14 Claims, 4 Drawing Sheets

Specification includes a Sequence Listing.

(56) References Cited

U.S. PATENT DOCUMENTS

| | | | |
|---|---|---|---|
| 2023/0227869 A1 | 7/2023 | Addy et al. | |
| 2023/0242950 A1 | 8/2023 | Addy et al. | |

FOREIGN PATENT DOCUMENTS

| | | | |
|---|---|---|---|
| JP | 2002529370 | A | 9/2002 |
| JP | 2003-532705 | A | 11/2003 |
| JP | 2007-528191 | A | 10/2007 |
| JP | 2013-520985 | T | 6/2013 |
| KR | 20010108111 | A | 12/2001 |
| WO | 199920224 | A2 | 4/1999 |
| WO | 1999037274 | A2 | 7/1999 |
| WO | 1990015127 | A1 | 12/1999 |
| WO | 2001072683 | A1 | 10/2001 |
| WO | 2005061686 | A1 | 7/2005 |
| WO | 2008092207 | A1 | 8/2008 |
| WO | 2011107977 | A1 | 9/2011 |
| WO | 2012106701 | A1 | 8/2012 |
| WO | 2012130961 | A1 | 10/2012 |
| WO | 2014140392 | A1 | 9/2014 |
| WO | 2016100957 | A1 | 6/2016 |

OTHER PUBLICATIONS

Sarah M. Meunier, "Development of a Packed-bed Reactor Containing Supported Sol-gel Immobilized Lipase for Transesterification," A thesis presented to the Univ. of Waterloo (2012).

Roberta Claro da Silva et al., "Interesterification of Lard and Soybean Oil Blends Catalyzed by Immobilized Lipase in a Continuous Packed Bed Reactor," J. Am. Oil Chem. Soc., vol. 88, p. 1925-1933 (2011).

Roberta Claro da Silva et al., "Microstructure and Thermal Profile of Structured Lipids Produced by Continuous Enzymatic Interesterification," J. Am. Oil Chem. Soc., vol. 90, p. 631-639 (2013).

Ozmutlu et al., "Numerical Simulation of Fluid Flow and Enzyme Catalysed Substrate Conversion in a Packed-bed Enzyme Reactor," Proc. Appl. Math. Mech. 3, p. 398-399 (2003).

X. Xu et al., "Production of Specific-Structured Lipids by Enzymatic Interesterification in a Pilot Continuous Enzyme Bed Reactor," AOCS, vol. 75, No. 11 (1998).

Xuebing Xu et al., "Production of Structured Lipids in a Packed-Bed Reactor with Thermomyces lanuginosa Lipase," AOCS, vol. 79, No. 6 (2002).

"Design of Ideal Plug Flow Reactors (PFRs) operated at Steady State under Isothermal Conditions," CP303, Set #4 (Jul.-Oct. 2013).

"Fixed-Bed Catalytic Reactors," Copyright 2011 by Nob Hill Publishing, LLC.

Neha R. Sonare et al., "Transesterification of used sunflower oil using immobilized enzyme," Journal of Molecular Catalysis B: Enzymatic 66, p. 142-147 (2010).

Steinke et al., "High-yield Preparation of Wax Esters via Lipase-catalyzed Esterification Using Fatty Acids and Alcohols from Crambe and Camelina Oils", J. Agric Food Chem, Feb. 2001, vol. 49, No. 2, pp. 647-651.

Jackson, Michael A., Isolation of Long-chain Aliphatic Alcohols From Beeswax Using Lipase-catalyzed Methanolysis in Supercritical Carbon Dioxide, Journal of Supercritical Fluids, vol. 37, 2006, pp. 173-177.

Lei, Qiong, et al., Functional Monoesters of Jojoba Oil can be Produced by Enzymatic Interesterification: Reaction Analysis and Structural Characterization, European Journal of Lipid Science and Technology, vol. 117, Dec. 22, 2014, pp. 630-636.

Extended European Search Report, European Patent Application No. 15871261.2, Jun. 8, 2018, 9 pages.

Steinke et al. 2000. Lipase-Catalyzed Alcoholysis of Crambe Oil and Camelina Oil for the Preparation of Long-Chain Esters. JAOCS, vol. 77, No. 4, pp. 361-366. (Year: 2000).

Gunawan et al., 2004. Lipase-Catalyzed Synthesis of Palm-Based Wax Esters. Journal of Oleo Science 2004, vol. 53, No. 10, pp. 471-477. (Year: 2004).

Aluyor et al. 2008. The use of antioxidants in vegetable oils—A review. African Journal of Biotechnology vol. 7, pp. 4836-4842. (Year: 2008).

Busson-Breysse, Jojoba Wax: Its Esters and Some of Its Minor Components, JAOCS, vol. 71, No. 9 (Sep. 1994).

Fucosterol, Fucosterol, CAS Entry, Cayman Chemical, 2019.

Sauer and Adkins, 1937. The Selective Hydrogenation of Unsaturated Esters to Unsaturated Alcohols. Journal of the American Chemical Society, vol. 59, No. 1, pp. 1-3. (Year: 1937).

Schuchardt, Transesterification of Vegetable Oils: a Review, J. Braz. Chem. Soc. vol. 9, No. 1, 199-210, 1998 (Year: 1998).

Oleyl-Alcohol, Oleyl Alcohol, CAS No. 143-28-2, Cayman Chemical Data Sheet, 2021, (Year: 2021).

De Greyt et al., Developments in Edible Oil Modification for the Production of Trans-free Food Fats, Oil Palm Bulletin, vol. 61, Nov. 1, 2010 (Nov. 1, 2010), pp. 38-44.

Wolfmeier et al., Waxes, Ullmann's Encyclopedia of Industrial Chemistry, Jun. 15, 2000 (Jun. 15, 2000), Wiley-VCH Verlag, Weinheim, XP055033858, pp. 111-172.

Barbara Fitch Haumann. Tools: hydrogenation, interesterification, 5 Inform 668 (Jun. 1994).

Melanie Cummins et al. A natural alternative, reprinted from Soap, Perfumery, and Cosmetics (SPC) Asia, (May 1, 1999) available at https://www.floratech.com/PDFs/Articles_MKT/ART15.pdf.

Personal Care Products Council. International Cosmetic Ingredient Dictionary and Handbook (14th ed. 2009).

A. Proskova et al., "Lipase-catalyzed transesterification of rendering plant fat," Res. Agr. Eng., vol. 56, No. 3: p. 122-125 (2010).

Elisa d'Avila Cavalcanti-Oliveira et al., "Study of Soybean Oil Hydrolysis Catalyzed by Thermomyces lanuginosus Lipase and Its Application to Biodiesel Production via Hydroesterification," Enzyme Research, Article ID 618692 (2011).

Novozymes Rethink Tomorrow, "Novozymes Lipozyme TL IM Handbook," available at least as early as Oct. 15, 2010.

E.J. Mammarella et al., "Predicting the Packed-Bed Reactor Performance with Immobilized Lactase," 2nd Mercosur Congress on Chemical Engineering, 4th Mercosure Congress on Process Systems Engineering, available at least as early as Mar. 15, 2005.

Naim M. Faqir et al., "Optimal Temperature Policy for Immobilized Enzyme Packed Bed Reactor Performing Reversible Michaelis-Menten Kinetics Using the Disjoint Policy," Chemical Engineering Department, The University of Jordan, Amman, and Chemical Engineering Department, Amman-College for Engineering Technology, Al-Balqa Applied University, Amman, Jordan, 2002 John Wiley & Sons, Inc.

Novozymes Food & Beverage, "Novozymes Lipozyme TL IM Handbook—Chapter 8—Ventilation, local exhaust, and vacuum cleaning systems," Novozymes A/S, 2010.

A.R. Memon et al., "Investigation of Phospholipase B Type Activity in Moringa oleifera Seeds," J.Chem.Soc.Pak. vol. 7, No. 1 (1985).

Hung-Min Chang et al., "Optimized synthesis of lipase-catalyzed biodiesel by Novozym 435," J Chem Technol Biotechnol 80:307-312 (2005).

Prof. Subhash Chand, "Enzyme Science and Engineering," Lecture-25 Non-Ideal Flow in Continuous Immobilized Enzyme Reactors, available at least as early Jan. 2013.

Mubarak Salyem Alsheraifi et al., "Design and Construction of a Lab-Scale System to Product Biodiesel from Waste Oil Using Immobilized Lipase," UAE University College of Engineering, available at least as early as Aug. 2006.

L. Woodcock et al., "Enzymatic synthesis of a Series of Alkyl Esters Using Novozyme 435 in a Packed-Bed, Miniaturized, Continuous Flow Reactor," Bioatalysis and Biotransformation, 26(6): 501-507 (Nov. -Dec. 2008).

Torben H. Ronne et al., "Enzymatic Interesterification of Butterfat with Rapeseed Oil in a Continuous Packed Bed Reactor," J. Agric. Food Chem., 53, 5617-5624 (2005).

Chapter 5: Immobilised Enzymes and their uses, available at least as early as Oct. 9, 2013.

Lene Fjerbaek et al., "A Review of the Current State of Biodiesel Production Using Enzymatic Transesterification," Institute of Chemical Engineering, Biotechnology and Environmental Technology, University of Southern Denmark, Published online Jan. 8, 2009.

(56) References Cited

OTHER PUBLICATIONS

"ADM Chooses a Trouble-Free Process for trans-Free Fats," Oil Mill Gazetteer, vol. 109 (Jun. 2004).
Jorn Borch Soe, "Enzymes for Degumming of Vegetable Oils," available at least as early as Oct. 2007.
"Oils & Fats," Novozymes' solutions effectively improve oil processing. (Oct. 17, 2013).
"Enzymes applications," Novozymes (Oct. 17, 2013).
"Today's Facts The World Leader in Bioinnovation," Novozymes A/S, 201-06395-01 (Aug. 2013).
"Choose Enzymes for a Trans Fat-Free Solution," Novozymes (2002).
"Oils & Fats—Production of concentrated fish oils with Novozymes Lipozyme 435," Novozymes A/S (2008).
"Oils & Fats—How to make PUFA ethanol esters," Novozymes A/S (2011).
"Eliminate trans fats from your bakery products," Novozymes A/S (2004).
"Cost-effective and simple—Edible fat production," Novozymes A/S (2002).
"Increase yields and save costs with enzymatic degumming," Novozymes A/S (2002).
Hongyong Fu et al., "Physical Characterization of Sorbitol or Glycerol Containing Aliphatic Copolyesters Synthesized by Lipase-Catalyzed Polymerization," Macromolecules, 36, 9804-9808 (2003).
T. Chaiyaso et al., "Biocatalytic acylation of carbohydrates with fatty acids from palm fatty acid distillates," J Ind Microbiol Biotechnol 33: 338-342 (2006).
Yin Hoon Chew et al., "External mass transfer model for the hydrolysis of palm olein using immobilized lipase," Food and Bioproducts Processing 86, 276-282 (2008).
"Enzyme Engineering XIII," Ed. Jonathan S. Dordick and Alan J. Russell, Annals of the New York Academy of Sciences, Oct. 1996.
Wim De Greyt et al., "Chemical vs. Enzymatic Interesterification," IUPAC-AOCS Workshop on Fats, Oils & Oilseeds Analyses & Production (Dec. 2004).
M. Kowalska et al., "Application of Modified Fats by Enzymatic Interesterification in Emulsions," Ital. J. Food Sci., vol. 23 (2011).
Andrea Salis et al., "Wax esters synthesis from heavy fraction of sheep milk fat and cetyl alcohol by immobilised ipases," Journal of Molecular Catalysis B: Enzymatic 21, 167-174 (2003).
"Oils & Fats—Oil recovery from gums with Novozymes Lecitase Ulta," Novozymes A/S (2007).
"Determination of lipase/esterase activity, titration by the pH-stat method (KLU, LU-MM, LU-CA, KLU(LPAX), and KLU (LEX)," Novozymes A/S (2010).
"Food specialties—Novozymes Lecitase Ultra," Novozymes Switzerland AG (2002).
"Oils & Fats—Refining of vegetable oils—Improving the degumming yield," Novozymes A/S (2004).
"Immobilized lipase activity based on ester synthesis (Propyl Laurate Units, PLU)," Novozymes A/S (2011).
E. Schuster et al., "On the safety of Aspergillus niger—a review," published by Appl Microbiol Biotechnal, vol. 59, pp. 426-435 (2002).
"Biocatalysis—Enzymes for organic synthesis," Novozymes A/S (2004).
Nevena Lukovic et al., "Biodiesel Fuel Production by Enzymatic Transesterification of Oils: Recent Trends, Challenges and Future Perspectives," Dr. Maximino Manzanera (Ed.), ISBN: 978-953-307-372-9, InTech (2011).
Lene Fjerbaek et al., "A Review of the Current State of Biodiesel Production Using Enzymatic Transesterification," Published online Jan. 8, 2009 at www.interscience.wiley.com (2009).
W.D. Cowan et al., "The Influence of lipase type and fat origin on Enzymatic Interesterification," Novozymes A/S (2008).
Kathryn D. Lardizabal et al., "Purification of a Jojoba Embryo Wax Synthase, Cloning of its cDNA, and Production of High Levels of Wax in Seeds of Transgenic Arabigopsis," Plant Physiology, vol. 122, pp. 645-655 (2000).
Thomas K. Miwa, "Structural Determination and Uses of Jojoba Oil," J. Amer. Oil Chem. Soc., vol. 61, No. 2, p. 407-410 (Feb. 1984).
David J. Sessa, "Derivation of a Cocoa Butter Equivalent from Jojoba Transesterified Ester via a Differential Scanning Calorimetry Index," J. Sci. Food Agric., v. 72, p. 295-298 (1996).
Sessa et al., "Differential Scanning Calorimetry Index for Estimating Level of Saturation in Transesterified Wax Esters," J. Amer. Oil Chem. Soc., v. 73, 271-273 (1996).
James Brown et al., "Trans Isomers in Cosmetics," Part 2, Soap & Cosmetcs, May 2001, p. 33-36, and Jun. 2001.
James Brown et al., "Trans Isomers in Cosmetics," Soap & Cosmetcs, May and Jun. 2001.
Patrick Cappillino et al., "Composition of Chilean Jojoba Seed," presentation given at the 5th New Crops Symposium in Atlanta, GA Nov. 10-13, 2001.
Patrick Cappillino et al., "Composition of Chilean Jojoba Seeds," Ind. Crops and Prod., v. 17, p. 177-182 (2003).
Junzo Otera. Transesterification, 93 Chem. Rev. 1449 (1993).
Eleonora Ledochowska et al. Comparison of the oxidative stability of chemically and enzymatically interesterified fats, 100 FETT/LIPID 343 (1998).
S. Hari Krishma et al. Lipases and Lipase Catalyzed Esterification Reactions In Nonaquenous Media, 44 Catalysis Revs. 499 (2002).
Xuebing Xu. Engineering of enzymatic reactions and reactors for lipid modification and synthesis, 105 Eur. J. Lipid Schi. Tech. 289 (2003).
Arnoldo Lopez-Hernandez et al. Lipase-catalyzed Transesterification of Medium-chain Tricyglycerols and a Fatty Hydrogenated Soybean Oil, 70 J. Food Sci. C365 (Jul. 13, 2005).
Cristina Otero et al. Continuous Enzymatic Transesterification of Sesame Oil and a Fully Hydrogenated Fat Effects of Reaction Conditions on Product Characteristics, 94 Biotech. & Bioeng'G 877 (2006).
X, Xu et al. Chemical and enzymatic interesterification of lipids for use in food, in Modifying lipis for use in food 234 (Frank D. Gunstone, ed., 2006).
Jamshid Farmani et al. Trans-free Iranian vanaspati through enzymatic and chemical transesterification of triple blends of fully hydrogenated soybean, rapeseed and sunflower oils, 102 Food Chem. 827 (2007).
Manuel Criado et al. Enzymatic interesterification of olive oil with fully hydrogenated palm oil: Characterization of fats, 110 Eur. J. Lipid Sci. Tech. 714 (2008).
Raquel Costales-Rodriguez et al. Chemical and Enzymatic Interesterification of a Blend of Palm Stearin: Soybean Oil for Low trans-Margarine Formulation, 86 J. Am. Oil Chemists' Soc. 681 (2009).
Tiankui Yang et al. Applications of Immobilized Thermomyces languinosa Lipase in Interesterification, 80 J. Am. Oil Chemists' Soc. 881 (2003).
Complaint for Patent Infringement, filed in *Cargill, Incorporated and International Flora Technologies LTD.*, Plaintiffs, v. *Vantage Specialty Chemicals, Inc.*, Defendant, Case 1:22-cv-00979-UNA, Doc. 1, File Jul. 26, 2022, pp. 1-38.
T. Haryati et al., "Determination of Iodine Value of Palm Oil Based on Triglyceride Composition", JAOCS, vol. 75, No. 7, 1998, pp. 789-792.
ASTM Int'l, Designation: D5554-95, "Standard Test Method for Determination of the Iodine Value of Fats and oils", (Reapporved 2006), pp. 1-3.
Am. Oil Chemist' Soc., AOCS Recommended Practice Cd 1c-85, Reapporved 2009, "Official Methods and Recommended Practiced of the AOCS", Sixth Edition (David Firestone, ed. 2013), pp. 1-3.
Richard D. O'Brien, Fats and Oils, "Formulating and Processing for Applications", CRC Press, 3rd ed, 2009, coverage, preface, p. 214-215, pp. 1-4.
David Firestone, Editor, "Physical and Chemical Characteristics of Oils, Fats, and Waxes", 3rd Ed., AOCS Press, (2013), coverage, preface, toc, pp. 1-3.
Final Report of the Cosmetic Ingredient Review, Expert Panel, "Safety Assessment of Simmondsia Chinensis (Jojoba) Seed Oil, Simmondsia Chinensis (Jojoba) Seed Wax, Hydrogenated Jojoba

(56) References Cited

OTHER PUBLICATIONS

Oil, Hydrolyzed Jojoba Esters, Isomerized Jojoba Oil, Jojoba Esters, Simmondsia Chinensis(Jojoba) Butter, Jojoba Alcohol, and Synthetic Jojoba Oil" (Sep. 23, 2008) available at https://www.cirsafety.org/ingredient/simmondsia-chinensis-jojoba-seed-oil, pp. 1-37.

Gupta et al., "Determination of Iodine Numbers of Edible Oils", Biochemical Education 22(1) 1994, p. 47.

Ernesto Hernandez, Ph.D., "Modification Technologies for Vegetable Oils". Omega Protein Inc., Practical Short Course on Vegetable Oil Processing and Products, Texas A&M University, Oct. 7-11, 2012, pp. 1-56.

Kuo, et al., "High Yield of Wax Ester Synthesized from Cetyl Alcohol and Octanoic Acid by Lipozyme RMIM and Novozym 435", Int. J. Mol. Sci. 2012, 13, 11694-11704, doi:10.3390/ijms130911694.

X. Xu et al., "Parameters Affecting Diacylglycerol formation During the Production of Specific-Structured Lipids by Lipase-Catalyzed Interesterification", JAOCS, vol. 76, No. 2 (1999), pp. 175-181.

X. Xu et al., "Pilot Batch Production of Specific-Structured lipids by lipase-Catalyzed Interesterification: Preliminary Study on Incorporation and Acyl Migration", JAOCS, vol. 75, No. 2 (1998), pp. 301-308.

De Clercq et al., "Enzymatic Interesterification of Palm Oil and Fractions: Monitoring the Degree of Interesterification using Different Methods", J Am Oil Chem Soc (2012) 89:219-229, DOI 10.1007/s11746-011-1905-x.

Answer and Demand for Jury Trial, filed in *Cargill, Incorporated and International Flora Technologies LTD.*, Plaintiffs, v. *Vantage Specialty Chemicals, Inc.*, Defendant, Case 1:22-cv-00979-UNA, Doc. 8, Filed Sep. 16, 2022, pp. 1-15.

E. Jurado, et al. "Kinetic model for the enzymatic hydrolysis of tributyrin in O/W emulsions," Chemical Engineering Science 61, p. 5010-5020 (2006).

Lori Gregg, Lipozyme CalB L, A lipase preparation produced by Aspergillus niger expressing a gene encoding a lipase from Candida antarctica, Novozymes, Oct. 2004, p. 1-20.

Schmid, et al. "Lipases: Interfacial Enzymes with Attractive Applications" Agnew. Chem. Int. Ed. 37:1608-1633 (1998).

G. Knothe, "Structure indices in FA chemistry. How relevant is the iodine value?" JAOCS, 79 (9) 847-854 (2002).

Sharma, et al. "Textbook of Cosmetic Formulations", https://www.researchgate.net/publication/325023106, pp. 1-94, May 2018.

Castillo, et al. "Medium-engineering: a useful tool for modulating lipaseactivity and selectivity", Biocatalysis, vol. 1 pp. 178-188 (2015).

Grand View Research, Inc. "Personal Care Specialty Ingredients MarketSize, Share, & Trends Analysis Report By Product (Active, Inactive), By Application (Skin Care, Hair Care, Oral Care, Color Cosmetics, Others), By Region, And Segment Forecasts, 2023-2030", https://www.grandviewresearch.com/industry-analysis/personal-carespecialty-ingredients-market, pp. 1-8 (2023).

National Academy of Sciences, "Biobased Industrial Products: Priorities for Research and Commercialization Priorities" Committee on Biobased Industrial Products, National Research Council, ISBN: 0-309-52185-8, pp. 1-162 (2000).

Covestro, "End-of-Life Myths and Facts about Cosmetic Ingredients" https://solutions.covestro.com/en/highlights/articles/stories/2019/biodegadability-andcosmetics#:~:text=Only%20natural%20products%20can%20biodegrade,nature%20and%20are%20easily%20biodegradable, pp. 1-2 (2023).

Wilford, "Oil From a Shrub Found in Desert May Save the Sperm Whale", The New York Times, https://www.nytimes.com/1975/05/15/archives/oil-from-a-shrub-foundin-desert-may-save-the-sperm-whale.html, pp. 1-5, May 15, 1975.

Saldana, et al. "Oxidative Stability of Fats and Oils Measured by Differential Scanning Calorimetry for Food and Industrial Applications", Applications of Calorimetry in a Wide Context, Chapter 19; pp. 445-474 (2013).

Gomna, et al. "Review of vegetable oils behaviour at high temperature for solar plants: Stability, properties and current applications" https://www.sciencedirect.com/science/article/pii/S0927024819302855, pp. 1-52 (2019).

Wen, et al. "Plant protein-derived antioxidant peptides: Isolation, identification, mechanism of action and application in food systems: A review" Trends in Food Science & Technology 105 (2020) pp. 308-322.

Excerpts, Smith, et al. "March's Advanced Organic Chemistry" Sixth Edition, Wiley-Interscience, coverpages and pp. 425-426, 2007.

Gad, et al. "Jojoba Oil: An Updated Comprehensive Review on Chemistry, Pharmaceutical Uses, and Toxicity", Polymers (Basel), 13(11): 1711; Jun. 2021.

Faller, "UCD Biophysics 241: Membrane Biology" LibreTexts, https://phys.libretexts.org/Courses/University_of_California_Davis/UCD%3A_Biophysics_241_-_Membrane_Biology, pp. 1-287, compiled Oct. 11, 2023.

Jadhav, et al. "Triglycerides of medium-chain fatty acids: a concise review," J Food Sci Technol (Aug. 2023) 60(8):2143-2152.

Casas-Godoy, et al. "Lipases: An Overview", Chapter 1, Lipases and Phospholipases. Methods in Molecular Biology, vol. 861. Humana Press., pp. 3-38 (2018).

Sharma, et al. "A Review on Applications of Microbial Lipases" International Journal of Biotech Trends and Technology (IJBTT) vol. 6, Issue 4, DOI : 10.14445/22490183/IJBTT-V19P601, pp. 1-5, (2016).

Rozenaal, "Interesterification of oils and fats", Inform, vol. 3, No. 11, cover pages and pp. 1232-1237, Nov. 1992.

Arumugam, et al. "Production of biodiesel by enzymatic transesterification of waste sardine oil and evaluation of its engine performance", Heliyon 3, article No. e00486, doi: 10.1016/j.heliyon.2017.e00486, pp. 1-18 (2017).

Dias Ribeiro, et al. "Production and Use of Lipases in Bioenergy: A Review from the Feedstocks to Biodiesel Production", SAGE-Hindawi Access to Research, Enzyme Research, vol. 2011, article id 615803, doi:10.4061/2011/615803, pp. 1-16 (2011).

Rauwerdink, et al. "How the Same Core Catalytic Machinery Catalyzes 17 Different Reactions: the Serine-Histidine-Aspartate Catalytic Triad of a/B-Hydrolase Fold Enzymes", ACS Catal., 5, 6153-6176 (2015).

Utama, et al. "Lipase-Catalyzed Interesterification for the Synthesis of Medium-Long-Medium (MLM) Structured Lipids—A Review", Food Technology and Biotechnology, vol. 57, No. 3, pp. 305-318 (2019).

Lewis, et al. "Biochemistry, Proteins Enzymes", StatPearls, NCBI Bookshelf, https://www.ncbi.nlm.nih.gov/books/NBK554481/?report=printable, Apr. 24, 2023, 4 pages.

Stergiou, et al. "Advances in lipase-catalyzed esterification reactions", Biotechnology Advances 31, 1846-1859 (2013).

Houde, et al. "Lipases and Their Industrial Applications", Applied Biochemistry and Biotechnology, vol. 118, pp. 155-170 (2004).

Berglund, "Controlling lipase enantioselectivity for organic synthesis", Biomolecular Engineering, vol. 18, 13-22 (2001).

Bornscheuer, "Methods to increase enantioselectivity of lipases and esterases", Chemical biotechnology, pp. 543-547 (2002).

Tabee, et al. "Effects of a-Tocopherol on Oxidative Stability and Phytosterol Oxidation During Heating in Some Regular and High-Oleic Vegetable Oils", J Am Oil Chem Soc., 85:857-867 (2008).

Khan, et al. "Current developments in esterification reaction: A review on process and Parameters" Journal of Industrial and Engineering Chemistry, 103, 80-101 (2021).

Arquette, "Effects of Additives on the Oxidative Stability of Botanical Emollients", International Flora Technologies, Ltd., SCC Ontario Chapter—Education Day, 54 pgs, Sep. 10, 1998.

Libre Texts, "26.8: Triglycerides", https://chem.libretexts.org/Bookshelves/Introductory_Chemistry/Introductory_Chemistry_(CK-12)/26%3A_Biochemistry/26.08%3A_Triglycerides, pp. 26.8.1-26.8.2, last accessed Dec. 5, 2023.

Biochemistry Free For All, Version 1.3, Oregon State University, Section 4.3: Mechanisms of Catalysis, (2018) pp. 380-394.

(56) References Cited

OTHER PUBLICATIONS

FDA, "Are All 'Personal Care Products' Regulated as Cosmetics?" https://www.fda.gov/industry/fda-basics-industry/are-all-personal-careproducts-regulated-cosmetics, 1 pg, Jun. 16, 2022.
Carli, "Cosmetic Formulations: A Beginners Guide", Institute Of Personal Care Science; coverpages, I-IV, and 1-118 (2020).
Karupaiah, et al. "Effects of stereospecific positioning of fatty acids in triacylglycerol structures in native and randomized fats: a review of their nutritional implications", Nutrition & Metabolism, 4:16, pp. 1-17 (2007).
Pleiss, et al. "Anatomy of lipase binding sites: the scissile fatty acid binding site", Chemistry and Physics of Lipids, 93 67-80 (1998).
Salvi, Chapter 4, "Transesterification methods", Production of Biodiesel from Non-Edible Sources, doi: https://doi.org/10.1016/B978-0-12-824295-7.00005-X, pp. 117-151 (2022).
Brown, et al. "Trans Isomers in Cosmetics Parts 1 and 2", Reprinted from Soap & Cosmetics (May & Jun. 2001) pp. 8, available at https://www.floratech.com/PDFs/Articles_MKT/ART17.pdf.
Brown, et al. "Trans Isomers in Cosmetics", ("Trans Isomers 1") Soap & Cosmetics, at 33, Business Insights: Global, pp. 1-5 (May 2001).
Brown, et al. "Trans Isomers in Cosmetics Part 2", ("Trans Isomers 2") Soap & Cosmetics, at 44, Business Insights:Global, pp. 1-6 (Jun. 2001).
Ditte Sidelmann Brinch, et al. "Summary of Toxicity Data, Candida B Lipase" Novozymes, Mar. 2004, coverpage, index, and p. 3-9.
Ahern et. al, Oregon State University, BioChemistry Free For All, LibreTexts, "4.3: Mechanisms of Catalysis", https://batch.libretexts.org/print/Letter/url=https://bio.libretexts.org/Bookshelves/Biochemistry/Book%3A_Biochemistry_Free_For_All_(Ahern_Rajagopal_and_Tan)/04%3A_Catalysis/4.03%3A_Mechanisms_of_Catalysis.pdf, (text last compiled on Jan. 1, 2024) p. 4.3.1-4.3.10.
Watson, "13 Reasons to Add Jojoba Oil to Your Skin Care Routine", healthline, 2023, retrieved from: https://www.healthline.com/health/beauty-skin-care/jojoba-oil-for-face. (Year: 2023).
Deng Li, et al. "Synthesis of Wax Esters by Lipase-catalyzed Esterification with Immobilized Lipase from Candida sp. 99-125*", Catalysis, Kinetics and Reactors, Chinese Journal of Chemical Engineering, 19(6), 978-982 (2011).
Hills Geoffrey, "Industrial use of lipases to produce fatty acid esters", Eur. J. Lipid Sci. Technol. 105 (2003) 601-607 DOI 10.1002/ejlt.200300853.
Zoete et al., "Ammonolysis of Carboxylic Esters, Catalyzed by Lipases", Laboratory of Organic Chemistry and Catalysis, Annals of the New York Academy of Sciences, Oct. 1996, 346-350, https://doi.org/10.1111/j.1749-6632.1996.tb33224.x.
Kirk-Othmer Concise Encyclopedia of Chemical Technology, Fourth Edition, Wiley-Interscience Publication, "Esters, Organic" (1999), cover pages, pp. 763-765, and index p. 2190, total 8 pgs.
IPR2023-00589, Judgment, Final Written Decision (*Vantage v. Cargill*), dated Sep. 5, 2024, pp. 85.
Junzo Otera, "Transesterification", Chem. Rev. 1993, 93, pp. 1449-1470.

* cited by examiner

SEQUENCE LISTING

```
Sequence total quantity: 2
SEQ ID NO: 1            moltype = AA  length = 342
FEATURE                 Location/Qualifiers
source                  1..342
                        mol_type = protein
                        organism = Candida antarctica
SEQUENCE: 1
MKLLSLTGVA GVLATCVAAT PLVKRLPSGS DPAFSQPKSV LDAGLTCQGA SPSSVSKPIL   60
LVPGTGTTGP QSFDSNWIPL STQLGYTPCW ISPPPFMLND TQVNTEYMVN AITALYAGSG  120
NNKLPVLTWS QGGLVAQWGL TFFPSIRSKV DRLMAFAPDY KGTVLAGPLD ALAVSAPSVW  180
QQTTGSALTT ALRNAGGLTQ IVPTTNLYSA TDEIVQPQVS NSPLDSSYLF NGKNVQAQAV  240
CGPLFVIDHA GSLTSQFSYV VGRSALRSTT GQARSADYGI TDCNPLPAND LTPEQKVAAA  300
ALLAPAAAAI VAGPKQNCEP DLMPYARPFA VGKRTCSGIV TP                     342

SEQ ID NO: 2            moltype = AA  length = 291
FEATURE                 Location/Qualifiers
source                  1..291
                        mol_type = protein
                        organism = Thermomyces lanuginosus
SEQUENCE: 2
MRSSLVLFFV SAWTALASPI RREVSQDLFN QFNLFAQYSA AAYCGKNNDA PAGTNITCTG   60
NACPEVEKAD ATFLYSFEDS GVGDVTGFLA LDNTNKLIVL SFRGSRSIEN WIGNLNFDLK  120
EINDICSGCR GHDGFTSSWR SVADTLRQKV EDAVREHPDY RVVFTGHSLG GALATVAGAD  180
LRGNGYDIDV FSYGAPRVGN RAFAEFLTVQ TGGTLYRITH TNDIVPRLPP REFGYSHSSP  240
EYWIKSGTLV PVTRNDIVKI EGIDATGGNN QPNIPDIPAH LWYFGLIGTC L           291
```

PROCESSES AND SYSTEMS FOR CATALYTIC MANUFACTURE OF WAX ESTER DERIVATIVES

CROSS REFERENCE TO RELATED APPLICATIONS

This application is a continuation of U.S. patent application Ser. No. 17/456,166, filed Nov. 23, 2021, which is a continuation of U.S. patent application Ser. No. 14/578,075, filed Dec. 19, 2014, now U.S. Pat. No. 11,248,245, issued Feb. 15, 2022, each of which is incorporated by reference herein in its entirety.

SEQUENCE LISTING

This document contains the material in and hereby incorporates entirely herein by reference the sequence listing file in XML format filed herewith named FloraTech109.xml, created Jan. 24, 2023, which is 3409 bytes in size.

BACKGROUND

1. Technical Field

Aspects of this document relate generally to systems and processes for reacting and processing wax esters and wax ester derivatives.

2. Background Art

A wax ester is formed from the chemical reaction of a fatty acid and a fatty alcohol, which results in the formation of an ester group that links two carbon chains. Wax esters are found in various animals and plants, including the jojoba plant (*Simmondsia chinensis*). Wax esters are used in various applications, including in cosmetic and personal care products.

SUMMARY

Implementations of processes for transesterifying wax esters may include: providing a feedstock including wax esters, contacting the feedstock with a lipase, and catalytically transesterifying the wax esters in the feedstock with the lipase to form a transesterified product. An oxidative stability index (OSI) of the transesterified product may be greater than an OSI of the feedstock.

Implementations of process for transesterifying wax esters may include one, all, or any of the following:

The transesterified product may include no methyl esters.

The feedstock may further include an antioxidant and catalytically transesterifying the wax esters in the feedstock with the lipase may further include catalytically transesterifying without one of removing and degrading the antioxidant in the feedstock.

The feedstock may further include a skin conditioning agent and a volatile compound and catalytically transesterifying the wax esters in the feedstock with the lipase may further include catalytically transesterifying without removing or degrading the skin conditioning agent and the volatile compound in the feedstock.

The wax esters of the feedstock may be jojoba wax esters.

The jojoba wax esters may further include hydrogenated jojoba wax esters.

A dropping point of the transesterified product may be greater than a dropping point of the feedstock and the dropping point may increase as a percentage of hydrogenated jojoba wax esters in the feedstock increases.

Implementations of a process for transesterifying wax esters may include providing a feedstock including wax esters, contacting the feedstock with a lipase, and catalytically transesterifying the wax esters in the feedstock with the lipase to form a transesterified product. The catalytic transformation may take place at greater than or equal to 98% yield.

Implementations of processes for transesterifying wax esters may include one, all or any of the following:

The transesterified product may include no methyl esters.

The feedstock may further include an antioxidant and catalytically transesterifying the wax esters in the feedstock with the lipase may further include catalytically transesterifying without removing or degrading the antioxidant in the feedstock.

The wax esters of the feedstock may be jojoba wax esters.

The jojoba wax esters may further include hydrogenated jojoba wax esters.

A dropping point of the transesterified product may be greater than a dropping point of the feedstock and the dropping point may increase as a percentage of hydrogenated jojoba wax esters in the feedstock increases.

Implementations of a process for transesterifying wax esters may include providing a feedstock including jojoba wax esters, contacting the feedstock with a lipase catalyst, and catalytically transesterifying the jojoba wax esters in the feedstock with the lipase to form a transesterified product. The yield of the catalytic transesterification may be greater than 4001 kilograms of product per kilogram of immobilized lipase catalyst.

Implementations of a process of transesterifying wax esters may include one, all, or any of the following:

The transesterified product may include no methyl esters.

The feedstock may further include an antioxidant and catalytically transesterifying the jojoba wax esters in the feedstock with the lipase may further include catalytically transesterifying without removing or degrading the antioxidant in the feedstock.

The feedstock may further include a skin conditioning agent and a volatile compound and catalytically transesterifying the jojoba wax esters in the feedstock with the lipase may further include catalytically transesterifying without removing or degrading the skin conditioning agent the skin conditioning agent and/or the volatile compound in the feedstock.

The jojoba wax esters may further include hydrogenated jojoba wax esters.

A dropping point of the transesterified product may be greater than a dropping point of the feedstock and the dropping point of the transesterified product may increase as a percentage of hydrogenated jojoba wax esters in the feedstock increases.

The catalytic transesterification may take place at a greater than or equal to 98% yield.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

Figure 1:
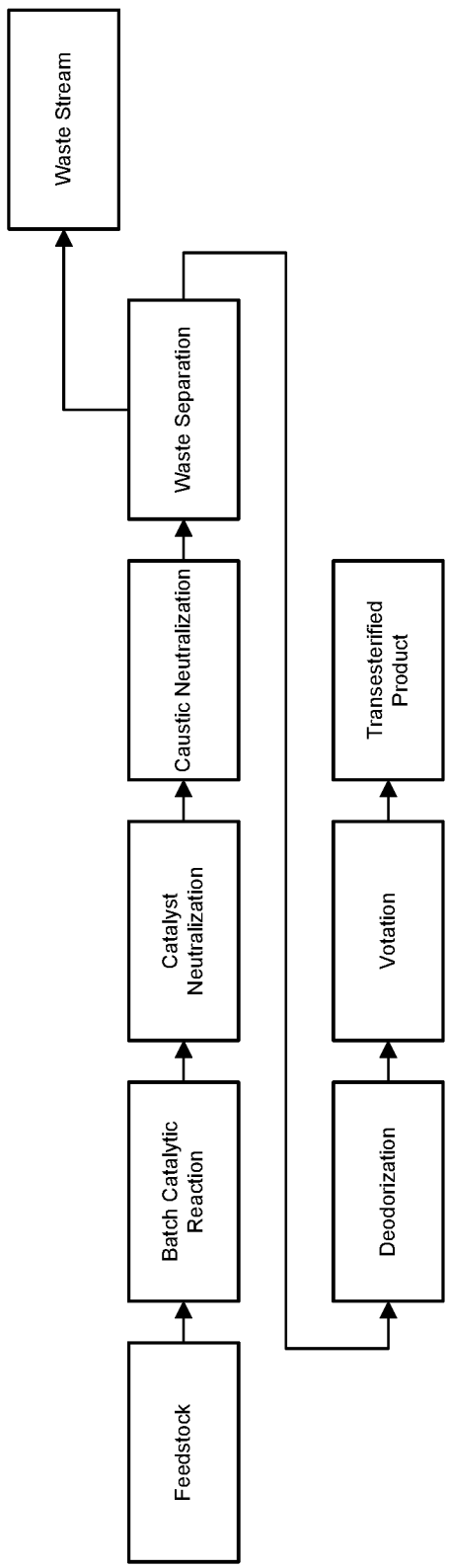
FIG. 1 is a flow chart of a conventional chemically catalyzed transesterification process.

This disclosure, its aspects and implementations, are not limited to the specific components, assembly procedures or method elements disclosed herein. Many additional components, assembly procedures and/or method elements known in the art consistent with the intended processes and systems for transesterifying wax esters will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such processes and systems for transesterifying wax esters, and other implementing components and methods, consistent with the intended operation and methods.

Transesterification involves the process of exchanging acyl groups located on each side of a ester group with an acyl group contained in an alcohol group, as illustrated below:

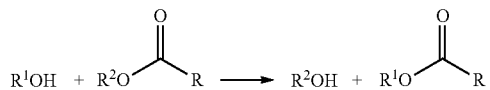

Transesterification for naturally occurring or structured or synthetic esters permits altering of various physical properties of the transesterified product when compared to the original feedstock. By non-limiting example, physical properties such as viscosity, dropping point, oil (oxidative) stability index (OSI), carbon chain distribution, and other properties of the transesterified product may be greater, equal to, or less than the corresponding values of the original wax ester-containing feedstocks. These changes take place at least in part because the chain lengths of the resulting ester products are randomized compared to the distribution in the original wax ester feedstock, which may alter the functionality of the transesterified material in a mixture and/or the thermal properties of the material.

Conventionally, transesterification of wax esters is accomplished using several different methods. Methods and systems for transesterifying jojoba oil that include the use of an acidic bentonite-type clay at temperatures between 150 C-350 C are disclosed in U.S. Pat. No. 4,329,298 to Brown, et al., entitled "Isomerization of Jojoba Oil and Products Thereof," filed Aug. 15, 1980 and issued May 11, 1982 and in U.S. Pat. No. 4,360,387 to Brown, et al., entitled "Isomorphous Jojoba Oil Compositions Containing Trans-Isomerized Jojoba Oil," filed Mar. 9, 1981, issued Nov. 23, 1982, the disclosures of both of which are hereby incorporated entirely herein by reference. When using the process described in the foregoing patents for transesterification, a 5%-10% loss of the original jojoba oil was observed.

Other conventional transesterification reactions use a chemical catalyst, such as sodium methylate (methoxide) or sodium hydroxide. While the reaction is catalytic, side reactions between the catalyst and components of the feedstock and/or reactants occur during transesterification process. These side reactions create byproducts that reduce the yield of the process and alter the properties of the transesterified product. Some of the property changes occur because of damage/changes to the feedstock esters caused by the high temperatures (100 C-230 C) and low pressures (<7 mmHg) required to carry out chemical catalytic transesterification. Other property changes occur because these conditions and/or the chemical catalysts themselves degrade, destroy, or reduce the effectiveness of other subcomponents of the wax ester feedstock. Where the wax ester feedstock is derived from a natural source, such as in a jojoba wax ester feedstock, existing antioxidants, sterols, hydrocarbons, and other volatile compounds (volatile in comparison to the volatility of the wax esters) react with the chemical catalyst in side reactions. The resulting transesterified product may have little or none of any of these components remaining intact following chemical catalytic transesterification and/or may reduce the effectiveness of these components. Furthermore, the transesterified product may include artifacts of these components which are undesirable or have undesirable effects in the product or subsequent mixtures that include the product.

Chemically catalyzed transesterification of wax esters is carried out in a batch reactor, and the catalyst cannot, accordingly, be recovered for reuse from the transesterification product. Referring to FIG. 1, a process flow diagram for a conventional transesterification process is illustrated. As illustrated, the feedstock containing wax esters is processed in a batch catalytic reaction. Following batch processing, the reaction is stopped using an acid and/or water such as citric acid to neutralize the remaining catalyst. At this point, the reactor contents are then checked for the presence of free fatty acids, which, if present requires the use of a neutralization process for the free fatty acids. The batch reactants are then moved into a waste separation step, in which the solution is washed with soft water to remove soaps and salts in the reactor material and separate them from the oil/lipid portion of the reactor material that contains the transesterified product to form a waste stream and a transesterified product stream. The transesterified product in the transesterified product stream is then bleached to remove remaining color bodies, soaps, and other undesirable byproducts formed during the chemically catalyzed transesterification reaction. The transesterified product stream is then deodorized and votated to produce a finished transesterified product. The process of votation is a controlled crystallization process or tempering process in which the transesterified product is agitated under controlled conditions to form a transesterified product with a desired consistency and crystalline structure for later use. Votation includes various heating, chilling, flash chilling, and other pressure adjustments to provide the desired consistency and/or structure.

In this document, various processes for transesterifying wax esters are disclosed that use enzymes to catalytically facilitate the transesterification reaction. In particular implementations, the enzymes are lipases, which are proteins that various biological organisms use to catalyze the hydrolysis and/or esterification of various compounds, such as lipids. As used herein, "lipase" means any enzyme or protein capable of being used in a transesterification reaction of a wax ester.

Figure 2:
FIG. 2 is a flow chart of an enzymatically catalyzed transesterification process.

Referring to FIG. 2, a process flow diagram for an enzymatically catalyzed transesterification process is illustrated. As illustrated, the wax ester feedstock passes through one or more catalytic reactors that allow a continuous catalytic transesterification reaction to take place. While it is possible to batch process wax ester feedstocks using enzymes, continuous processing has many well-known advantages over batch processing. Following the continuous catalytic transesterification reaction, the transesterified product is deodorized and votated to produce a finished transesterified product stream. As can be observed, there are fewer process steps in an enzymatically catalyzed transesterification process. Furthermore, as will be discussed in detail below, because there are little or no side reactions between the enzyme catalysts and the reactants, while the transesterification results of the enzyme catalyzed process are very similar to chemically catalyzed process, the properties and components of an enzyme catalyzed transesterified product stream differ in important ways while retaining essentially the same functional characteristics.

Figure 3:
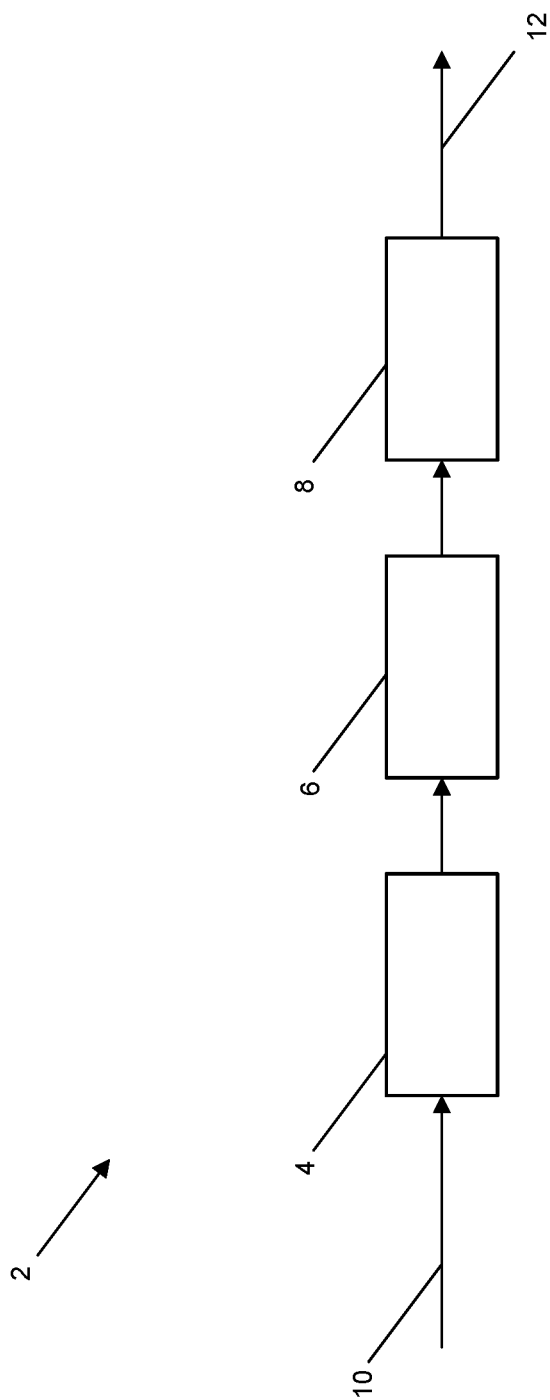
FIG. 3 is a process diagram showing an implementation of three enzymatically catalyzed transesterification reactors in series.

Referring to FIG. 3, a process flow diagram of an implementation of a continuous enzymatic reactor system 2 for enzymatic catalyzed transesterification of wax esters is illustrated. As illustrated, the system 2 includes three reactors 4, 6, 8 connected in series. Each reactor contains the enzyme and is designed to place the incoming wax ester feedstock 10 in contact with the enzyme. Following processing, the transesterified product 12 exits the final reactor 8 for subsequent processing/collection. In particular implementations, the enzyme is immobilized on a substrate material designed to facilitate interaction of the incoming wax ester feedstock. In other implementations, the enzyme is immobilized on the internal structure(s) of the reactor itself or is free flowing within the reactor system and recycled back to the reactor(s). In the implementation illustrated in FIG. 3, the reactors are packed bed reactors. Those of ordinary skill in the art will readily be able to select various reactor components and other piping, pumps, filters, and other process equipment to facilitate the use of the enzymatic reactors using the principles disclosed herein.

Many different enzymes may be employed in enzymatic catalytic transesterification reactions for wax esters, including those that are derived/obtained from biological organisms, those made synthetically, and those that are entirely artificial, whether made biologically and/or synthetically. For those enzymes that are lipases, these may include, one, some, any, or any combination of lipases derived from the following organisms: *Aspergillus niger*, *Aspergillus oryzae*, *Bacillus subtilis*, *Bacillus thermocatenulatus*, *Burkholderia cepacia*, *Burkholderia glumae*, *Candida rugosa*, *Candida antarctica* A, *Candida antarctica* B, *Candida cylindracea*, *Candida parapsilosis*, *Chromobacterium viscosum*, *Geotrichum candidum*, *Geotrichum* sp., *Mucor miehei*, *Humicola lanuginose*, *Penicillium camembertii*, *Penicillium chrysogenum*, *Penicillium roquefortii*, *Pseudomonas cepacia*, *Pseudomonas aeruginosa*, *Pseudomonas fluorenscens*, *Pseudomonas fragi*, *Pseudomonas alcaligenes*, *Pseudomonas mendocina*, *Rhizopus arrhizus*, *Rhizomucor miehe*, *Staphylococcus hyicus*, *Staphylococcus aereus*, *Staphylococcus epidermidis*, *Staphylococcus warneria*, *Staphylococcus xylosus*, *Thermomyces lanuginosus*, *Aspergillus* sp., *Bacillus* sp., *Burkholderia* sp., *Candida* sp., *Chromobacterium* sp., *Geotrichum* sp, *Mucor* sp, *Humicola* sp, *Penicillium* sp, *Pseudomonas* sp, *Rhizopus* sp., *Staphylococcus* sp, and *Thermomyces* sp.

In particular implementations, the lipase may be the following: a lipase from *Thermomyces lanuginosus* marketed under the tradenames LIPOZYME TL IM™ or LIPEX™ by Novozymes A/S of Bagsvaerd, Denmark and immobilized on a substrate also manufactured by Novozymes. A representative sequence listing of the lipase is included as SEQ ID NO: 1 herein. In other implementations, the lipase may be that marketed under the tradename NOVOZYM™ by Novozymes, A/S derived from *Candida antarctica*, a representative sequence listing for which is included as SEQ ID NO: 2 herein. In various implementations, the lipases may be any of the following: those marketed under the tradenames CALB L™, NOVOZYME 435™, NOVOCOR AD L™, and LIPOLASE 100L™ by Novozymes; those marketed under the tradenames CALB™, CALA™, and CRL™ by c-LEcta, GMBH of Leipzig, Germany; those marketed under the tradenames LIPASE A "AMANO" 12™, LIPASE AY "AMANO"™ 30SD™, LIPASE G "AMANO" 50™, LIPASE R "AMANO"™, LIPASE DF "AMANO" 15™, LIPASE MER "AMANO"™, and NEWLASE F™ by Amano Enzyme Inc. of Nagoya, Japan; those marketed under the tradenames LIPASE MY™, LIPASE OF™, LIPASE PL™, LIPASE PLC/PLG™, LIPASE QLM™, LIPASE QLC/QLG™, LIPASE SL™, and LIPASE TL™ by Meito Sangyo Co., Ltd., of Nagoya, Japan.

In other implementations, the lipase may be a lipase from *Candida antarctica* A, a lipase from *Candida antarctica* B, *Candida rugosa* or any combination thereof. In various implementations, the lipases may be any disclosed in U.S. Patent Application Publication No. 20140017741 (the '714 publication) to Nielsen, et al., entitled "Esterification Process," filed Oct. 1, 2013 and published Jan. 16, 2014, the disclosure of which is hereby entirely incorporated herein by reference. Those lipases disclosed in the sequence listings for the various patent applications listed in para. [0026]-[0029] in the '741 publication, previously incorporated by reference, each of which applications are hereby entirely incorporated by reference herein, may also be those utilized in particular implementations. In various implementations, the lipases may be those have at least 60%, at least 70%, at least 80%, at least 90%, at least 95%, at least 96%, at least 97%, at least 98%, or even at least 99% identity to any of the lipases disclosed herein, in the '714 publication, and in the patent applications disclosed in the '714 publication, all of which have been previously incorporated by reference.

A wide variety of wax esters may be processed using the enzymatic catalytic transesterification processes disclosed herein. By non-limiting example, wax esters contained in the following materials may be included in the wax ester feedstocks processed using the principles disclosed herein: beeswax, Chinese wax, shellac wax, whale spermaceti, lanolin, carnauba wax, ouricuri wax, jojoba oil, candelilla wax, esparto wax, Japan wax, rice bran oil, sunflower wax, ozocerite, ozokerite, and montan wax. Any other natural or synthetically produced wax esters may also be processed using the principles disclosed herein. Various examples are discussed in this document regarding wax esters in jojoba oil feedstocks, but these examples are merely given to illustrate the principles disclosed herein.

Jojoba oil derived from the seeds of the jojoba plant contains wax esters and other components that have been noted to be useful for various functions. These include steryl esters, sterols, and various hydrocarbons that can be useful as skin conditioning agents in cosmetics and personal care products. Antioxidants, like tocopherols, are also included, along with various volatile ingredients naturally present in the oil, which are volatile in comparison with the wax esters. The wax esters in jojoba oil generally vary between 34 and 48 carbons in length. A detailed analysis of the wax ester distribution, structural characteristics, and other components in jojoba oil may be found in the paper by Thomas K. Miwa, entitled "Structural Determination and Uses of Jojoba Oil," *J. Amer. Oil Chem. Soc.*, Vol. 61, No. 2 (February 1984), p. 407-410, the disclosure of which is hereby incorporated entirely herein by reference. It has been observed that jojoba oil derived from plants from South America, Israel, and North America differ somewhat in chemical composition, but these differences are slight and have not been observed to produce any effect on the product functional characteristics. Details on the composition of jojoba oil from Chile may be found in the article by Cappillino et al., entitled "Composition of Chilean Jojoba Seeds," *Ind. Crops and Prod.*, v. 17, p. 177-182 (2003), the disclosure of which is hereby incorporated entirely herein by reference. Additional information on the differences in jojoba oil produced from jojoba seeds from Chile, North America, Israel, and the rest of South America may be found in the presentation by Cappillino et al., "Composition of Chilean Jojoba Seed," given at the 5th New Crops Symposium in Atlanta, Ga. Nov. 10-13, 2001, a copy of which is included herewith at Appendix B, the disclosure of which is hereby incorporated entirely herein by reference.

Transesterification of jojoba oil has conventionally been done using the chemically catalyzed processes discussed herein. When such chemical catalyzed processes are used, side reactions form various fatty acid methyl esters and leave various free fatty alcohols when sodium methoxide is used. The resulting transesterified product stream may include 5% or less by weight of these fatty acid methyl esters, which may function as an emollient, and the free fatty alcohols, which may function as an emollient and viscosity controller. As was previously discussed however, the reaction of the chemical catalyst removes or degrades the steryl esters, sterols, tocopherols, hydrocarbons, and volatile ingredients in the jojoba oil. This degradation and/or removal of these components changes the functionality and physical properties of the transesterified product stream. In particular, the degradation and/or removal of the tocopherols and other naturally occurring antioxidants reduces the OSI of the transesterified product to below the OSI of the original jojoba oil. As jojoba oil includes between about 0 to about 500 ppm of tocopherols with the major component being gamma-tocopherol, elimination of the natural tocopherols has a significant effect on the oxidative stability of the mixture. An addition of 500 ppm of tocopherols can enhance the oxidative stability of the material by about 50% to about 200% of the original oxidative stability.

Table 1 lists some process parameters and some characteristics of the transesterified product stream for a chemically catalyzed transesterification process and those for an enzymatically catalyzed transesterification process.

TABLE 1

| Process Parameter | Chemical Catalyst | Enzymatic Catalyst |
| --- | --- | --- |
| Reaction Temperature | 100 C.-230 C. | 10 C.-70 C. |
| Reaction Pressure | <7 mm Hg | 760 mm Hg (ambient) |
| Product Color | Increased (changes color) | No changes |
| Soap Formation | Yes | No change |
| Transesterification Yield | 85%-95% | >98% |

Table 2 shows observed effect of the chemically catalyzed process and various enzymatically catalyzed processes on the various naturally present components in jojoba oil as well as side reaction byproducts.

TABLE 2

| Transesterified Product Component | Skin Care Formula Function | Chemical Catalyst | Enzyme Catalyst |
| --- | --- | --- | --- |
| Steryl Esters | Skin Conditioning Agent | Removed/ Degraded | Functionally Unaffected |
| Sterols | Skin Conditioning Agent | Removed/ Degraded | Functionally Unaffected |
| Tocopherols | Antioxidant | Removed/ Degraded | Functionally Unaffected |
| Hydrocarbons | Skin Conditioning Agent | Removed/ Degraded | Unchanged |
| Fatty Acid Methyl Esters | Emollient | Formed, <5% | Not formed |
| Free Fatty Alcohols | Emollient, Viscosity Controller | Formed, <5% | Not formed |
| Volatile Ingredients | Sensory Attributes | Removed/ Degraded | Functionally Unaffected |

As can be observed from the table, the enzymatic transesterification process takes place at the melting point of the jojoba oil (and any hydrogenated jojoba oil included in the feedstock) under substantially atmospheric pressure. The reaction also proceeds without removing/degrading the tocopherols or volatiles naturally contained in the jojoba oil. Also, the enzyme catalyzed process does not create methyl esters or free fatty alcohols which may limit the applications of the transesterified product as they affect the emollient and/or viscosity behavior of the product. Furthermore, the degradation/removal of the tocopherols in the chemically catalyzed process adversely affects the oxidative stability (measured by the OSI) and accordingly, the shelf life, of the transesterified product. The addition of fatty acid methyl esters creates different material spreading and refractive properties in the chemically transesterified product, even at levels up to about 5% by weight.

Several examples of chemically catalyzed transesterification reactions compared with enzymatically catalyzed transesterification reactions are disclosed in this document, including in FIGS. 4-7. These will be considered in turn.

EXAMPLE 1

Chemical Catalytic Batch Process vs. Enzymatically Catalyzed Batch Process

A 1 liter 3-necked glass flask equipped with an agitating blade was loaded with 800 g of refined jojoba oil. The oil was heated to 110 C and dried under vacuum for 30 minutes. After drying was completed, a small amount of sodium methylate (0.3% by weight) was added to the mixture. The transesterification reaction was agitated under vacuum at 120 C for two hours. The catalyst was then neutralized with 1 g of citric acid and then treated with a silica and bleaching clay mixture to remove color induced by the reaction and other residual impurities. The transesterified product was a yellow liquid.

A 2 liter jacketed glass reactor equipped with an agitating blade was loaded with 1.2 kg of refined jojoba oil and 48 g (4% by weight) of LIPOZYME TL IM™ (*Thermomyces lanuginosus* lipase) from Novozymes. A layer of nitrogen was blanketed over the oil and the mixture was agitated at ambient temperature. After five hours, the lipase was removed from the mixture and the jojoba derivative was analyzed. The transesterified product was a slightly yellow liquid similar in texture and color to the initial feedstock. Measurement of the wax ester distributions for the feedstock and both transesterified products was done using an Hewlett Packard GC 5980 Series II gas chromatograph with a Restek MxT-65TG 30 meter, 0.25 mm ID capillary chromatographic column with a Crossbond 65% diphenyl/35% dimethyl polysiloxane film thickness of 0.1 microns. The gas chromatograph has split/splitless injection and uses an FID detector. Operating parameters of the gas chromatograph were as follows: injection port: 300 C, detector: 325 C, split ratio: 100:1, 1 microliter injection with oven temperature ramping from 280 C to 350 C over 20 minutes. Helium carrier gas was used. The concentration of tocopherols was measured using HPLC rather than the gas chromatograph. The equipment used was an Agilent LC 1100 series with an autosampler, quaternary pump, diode array detector (DAD), and an Alltech 2000 ELSD operating with a drift tube temperature of 40.0° C. with 1.7 mL/min Nitrogen. The column used was an Agilent RX-SIL 4.6×50mm 1.8 um normal phase silica column kept at 40.0° C. The DAD was set to detect UV at wavelengths 210 nm and 295 nm to identify the optically active portion of the tocopherols as they eluted from the column. The mobile phase consisted of an isocratic flow of 98% hexane and 2% isopropanol at 0.5 mL/min with a total run time of 15.00 minutes. Table 3 summarizes the results of both experiments.

TABLE 3

|  | Feedstock Composition | Chemical Catalyst | % Change | Enzyme Catalyst | % Change |
|---|---|---|---|---|---|
| Components |  |  |  |  |  |
| Tocopherols | 0.04% | 0.00% | −0.04% | 0.04% | 0.00% |
| Fatty Acid Methyl Esters | 0.00% | 3.10% | 3.10% | 0.00% | 0.00% |
| Free Fatty Alcohols | 0.00% | 1.80% | 1.80% | 0.00% | 0.00% |
| OSI (hours) | 26.5 | 21.5 | −18.87% | 38.6 | 45.66% |
| Wax Ester Content | 98.00% | 93.10% | −4.90% | 98.00% | 0.00% |
| Wax Ester Distribution |  |  |  |  |  |
| C36:1 | 1.12% | 1.30% | 0.180% | 1.20% | 0.080% |
| C38:2 | 6.02% | 4.90% | −0.120% | 4.80% | −1.220% |
| C40:2 | 27.95% | 35.76% | 7.810% | 34.34% | 6.390% |
| C42:2 | 50.28% | 40.64% | −9.640% | 40.92% | −9.360% |
| C44:2 | 9.94% | 13.75% | 3.811% | 14.93% | 4.991% |
| C46:2 | 1.20% | 1.89% | 0.690% | 2.23% | 1.030% |

Examining the results shows that the formation of fatty acid methyl esters and free fatty alcohols in the chemically catalyzed transesterification reaction produces a product with a lower wax-ester percentage than the original starting material. The results also indicate that the chemically catalyzed reaction destroys the original amount of tocopherols present in the feedstock, which reduces the OSI of the transesterified product. Surprisingly, however, the OSI of the enzymatically catalyzed transesterified product is greater than that of the feedstock. This result indicates that the enzymatic catalysis has an unexpected positive effect on OSI that is not explainable simply by the enzymatic catalyst preserving the natural tocopherols originally present in the feedstock during the reaction. The OSI was measured using an Omnion Scientific Services machine, Model OSI-8-110, according to the procedures set forth in the American Oil Chemist's Society (AOCS) Official Method Cd 12b-92, a copy of which is submitted herewith as Appendix A and incorporated entirely herein by reference.

In all of the above examples, no significant difference in the viscosity between the chemically catalyzed and the enzymatically catalyzed transesterified products was observed.

The chemically catalyzed and enzymatically catalyzed transesterified products were tested for performance in a typical cream formulation. Each cream formulation used 3% by weight of each transesterified product (chemically or enzymatically catalyzed) created in the previous experiment. Table 4 shows the formulation details of the cream along with the components and suppliers. Following Table 4 is the mixing procedure used.

TABLE 4

| Phase | Tradename | International Nomenclature Cosmetic Ingredient (INCI) | Supplier | Weight percent % (of total) |
|---|---|---|---|---|
| A | Deionized Water | Water | — | 66.27 |
|  | VERSENE ™ Na2 Crystals | Disodium EDTA | The Dow Chemical Co. | 0.03 |
| B | Glycerin, USP | Glycerin | The Dow Chemical Co. | 5.00 |
|  | KELTROL CG-T ™ | Xanthan Gum | CP Kelco | 0.30 |
| C | FLORAMAC ™ Macadamia Oil. | *Macadamia integrifolia* seed oil. | Floratech | 3.00 |
|  | FLORAESTERS 30 ™ | Jojoba Esters (and) Tocopherol | Floratech | 3.00 |
|  | Transesterified Wax Esters | Jojoba Derivative being examined | — | 3.00 |

TABLE 4-continued

| Phase | Tradename | International Nomenclature Cosmetic Ingredient (INCI) | Supplier | Weight percent % (of total) |
|---|---|---|---|---|
| | Cocoa Butter | *Theobroma cacao* (Cocoa) seed butter | Cognis Corporation | 5.00 |
| | FLORASUN 90 ™ | *Helianthus annuus* (Sunflower) seed oil (and) Tocopherol | Floratech | 2.00 |
| | BOTANISIL CP-33 ™ | Cyclopentasiloxane | Botanigenics, Inc. | 4.00 |
| | DOW CORNING 200 ™ Fluid | Dimethicone | Dow Corning Corporation | 0.50 |
| | LEXEMUL 561 ™ | Glyceryl Stearate (and) PEG-100 Stearate | Inolex Chemicals | 4.00 |
| | EMULGADE PL ™ | Cetearyl Glucoside (and) Cetearyl Alcohol | Cognis Corporation | 3.00 |
| D | PHENONIP ™ | Phenoxyethanol (and) Methylparaben (and) Ethylparaben (and) Butylparaben (and) Propylparaben (and) Isobutylparaben | Clariant Corporation | 0.90 |
| | | | Total | 100 |

The cream was prepared as follows: Step 1: Dissolve the VERSENE™ Na2 crystals into the deionized water with stirring at 75 C to form phase A. Step 2: Mix the KELTROL CG-T™ in the glycerin USP to form phase B. Add phase A to phase B with rapid stirring to form phase AB. Step 3: Combine all ingredients of phase C and 75 C using propeller agitation. Add phase C to phase AB at 75 C using propeller agitation to form phase ABC. Step 4: Reduce the temperature of the cream to 50 C and add phase D to phase ABC with propeller agitation. Cool the batch with moderate agitation to room temperature.

Table 5 summarizes the viscosity and appearance differences between the two cream formulations. While a viscometer can be used to measure the viscosity of such materials, the test used to calculate the viscosities, a method of calculating the viscosity without a viscometer, includes placing a sample weighting 0.5 g on a piece of horizontally oriented paper and drawing a starting line immediately next to the sample. The paper is then oriented vertically for 30 seconds and then laid flat again. A line is then drawn at the edge of where the sample has finished flowing down the paper. A ruler is then used to measure the distance between the starting line and the ending line. By developing a calibration curve for this method using materials of known viscosity and measuring the length of travel down the paper, a correlation can be developed between the length of travel of the material and the viscosity of the material.

TABLE 5

| Transesterified Product Type in Cream | Viscosity | Appearance |
|---|---|---|
| Chemically Catalyzed | 120,900 cP | White, semi-solid phase |
| Enzymatically Catalyzed | 78,585 cP | White, liquid phase, glossy |

Table 5 indicates that the use of enzymatically catalyzed transesterified jojoba oil created a cream formulation that had a viscosity drop of nearly 35% from the viscosity of the chemically catalyzed cream. This data indicates that the enzymatically catalyzed transesterified jojoba oil has the functional effect of lowering the resulting product viscosity compared to chemically catalyzed product. The difference in appearance between the two cream formulations (i.e., the enzymatically catalyzed product having less shine and gloss when applied to a surface) is due the relative abundance of fatty acid methyl esters in the chemically catalyzed product.

EXAMPLE 2

Continuous Flow Enzymatically Catalyzed Transesterification Using Lipase

A 10 cm×100 cm stainless steel cylinder was filled with 0.5 kg of LIPOZYME TL IM™ immobilized on substrates. The cylinder was equipped with mesh screening material on both ends to secure the enzyme substrates and was sealed and conditioned by evacuating the catalyst of excess moisture and salts used in the enzyme manufacturing process. The cylinder was connected to a metering pump and a pressure gauge monitored by a solenoid that automatically shut down flow if the pressure at the entrance to the cylinder rose above 15 psi. Flow rate was calculated by the rate of conversion obtained from batch reactions using the same enzymatic catalyst and was 0.8 kg/hr. A stock of refined jojoba oil was fed to the reactor cylinder at a constant temperature and pressure, as the cylinder was submerged in a water batch to keep the reactor temperature constant. The resulting product exiting the cylinder was slightly yellow and liquid at room temperature. The properties of the transesterified product produced are summarized in Table 6.

TABLE 6

| Components | Feedstock Composition | Enzymatically Catalyzed | % Change |
|---|---|---|---|
| Tocopherols | 0.04% | 0.04% | 0.00% |
| Fatty Acid Methyl Esters | 0.00% | 0.00% | 0.00% |
| Free Fatty Alcohols | 0.00% | 0.00% | 0.00% |
| OSI (hours) | 26.5 | 36.2 | 36.6% |
| Wax Ester Content | 98% | 98% | 0% |
| Wax Ester Distribution | | | |
| C36:1 | 1.12 | 1.20 | 0.080% |
| C38:2 | 6.02 | 4.91 | −1.110% |
| C40:2 | 27.95 | 35.30 | 7.350% |
| C42:2 | 50.28 | 41.20 | −9.080% |
| C44:2 | 9.94 | 14.79 | 4.851% |
| C46:2 | 1.2 | 2.14 | 0.940% |

As can be observed, the continuous process created a fully randomized transesterified jojoba oil product that reached full conversion before exiting the reactor. Again, the increase in OSI from the feedstock material was again surprisingly noted. The transesterified product in this example was included in a cream formulation like that in Table 4 and similar visual appearance and viscosity results to the enzymatically catalyzed cream in Table 5 were observed.

EXAMPLE 3

Continuous Enzymatically Catalyzed Transesterification Using Jojoba Oil and Hydrogenated Jojoba Oil The same experimental system as in Example 2 was used but modified to operate at 70 C in order to maintain a homogenous feedstock mixture of j of oba oil and hydrogenated jojoba oil entering the reactor in the feedstock. Various additional background information on the structure, use, and of transesterification reactions using hydrogenated jojoba wax esters may be found in the articles by James Brown and Robert Kleiman "Trans Isomers in Cosmetics", Parts 1 and 2, *Soap & Cosmetics,* May 2001, p. 33-36 and June 2001, as well as in Sessa et al., "Differential Scanning calorimetry Index for Estimating Level of Saturation in Transeesterified Wax Esters," *J. Amer. Oil Chem. Soc.,* v. 73, 271-273 (1996), and David J. Sessa, "Derivation of a Cocoa Butter Equivalent from Jojoba Transesterified Ester via a Differential Scanning calorimetry Index," *J. Sci. Food Agric.,* v. 72, p. 295-298 (1996) the disclosures of all of which are hereby entirely incorporated herein by reference.

Because of the absence of unsaturated wax esters in the hydrogenated jojoba wax esters (HJW), the progress of the reaction can be measured by observing the formation of monounsaturated wax esters during the reaction. The dropping point, or the temperature at which the transesterified product transitions from a semi-solid to a liquid state, was also monitored. The dropping point was calculated using the method outlined in ASTM D127-63. The results of the processing, with a comparison to a feedstock containing no hydrogenated jojoba wax esters, are included in Table 7.

TABLE 7

| Components | Feedstock Composition | 0% HJW | 20% HJW | 30% HJW |
|---|---|---|---|---|
| Tocopherols | 0.04% | 0.04% | 0.04% | 0.04% |
| Fatty Acid Methyl Esters | 0.00% | 0.00% | 0.00% | 0.00% |
| Free Fatty Alcohols | 0.00% | 0.00% | 0.00% | 0.00% |
| Wax Ester Content | 98% | 98% | 98% | 98% |
| % Monounsaturated Wax Ester | 3 | 3 | 31.98 | 41.50 |
| % Conversion | N/A | 99.96% | 100.55% | 100.01% |
| Dropping Point (degrees C.) | 8 | 8 | 44 | 49 |

The percent conversion in Table 7 was calculated based on ideal monounsaturated wax ester values derived from the fatty acid and fatty alcohol proportions of the feedstock. These proportions (and the other wax ester distribution data in this document) were determined using the Hewlett Packard gas chromatograph disclosed herein and a solvent to solubilize the samples. During testing, approximately 1 drop of sample was diluted with 10 drops of solvent and 1.0 uL of the resulting mixture was injected into the gas chromatograph. Based on historical data for jojoba wax esters previously obtained and a theoretical randomization of the percentage of the various chain lengths (assuming all esters were transesterified), an ideal value for each wax ester species (i.e., C36:2, C42:2, etc.) can be determined. Since the C42:2 ester is the one that has the largest change from pre- to post-transesterification, it is the one used in Example 3 to monitor conversion of the reactants. The ideal percentage of C42:2 in pure jojoba oil is 41.28% following a complete and total randomization. Accordingly, the conversion of pure jojoba oil can be calculated as:

% Conversion HJW0=(% C42:2)/41.28×100

Where HJW0 is a jojoba oil feedstock that does not contain any hydrogenated jojoba wax esters. For the feedstocks that include hydrogenated jojoba oil and wax esters, the percent conversion is monitored by the formation of the monounsaturated species. The species monitored in these reactions include C38:1, C40:1, C42:1, C44:1, and C46:1. The same gas chromatographic procedures used in this document are used to monitor the various reactants during and following the transesterification reaction. Table 8 contains the ideal overall values for monounsaturated wax esters (representing all the individual species percentages added together) for a feedstock containing 20%, 30%, and 50% hydrogenated jojoba wax esters (HJW20, HJW30, and HJW50, respectively).

TABLE 8

| Product | Ideal % of Monounsaturated Wax Esters |
|---|---|
| HJW20 | 31.20 |
| HJW30 | 40.00 |
| HJW50 | 46.50 |

These values can be used to calculate the percent conversion of jojoba wax esters to the ideal mixture of monounsaturated wax esters given the percentage of the monounsaturated components by weight in the feedstock. The calculation is given as follows:

% Conversion=(% Monounsaturates)/(Ideal % Monounsaturates)×100

Because of the nature of the calculation it is possible for the calculation to be greater than 100% depending upon measurement results and the fact that the ideal number is based on historical average data for jojoba oil.

Figure 4:
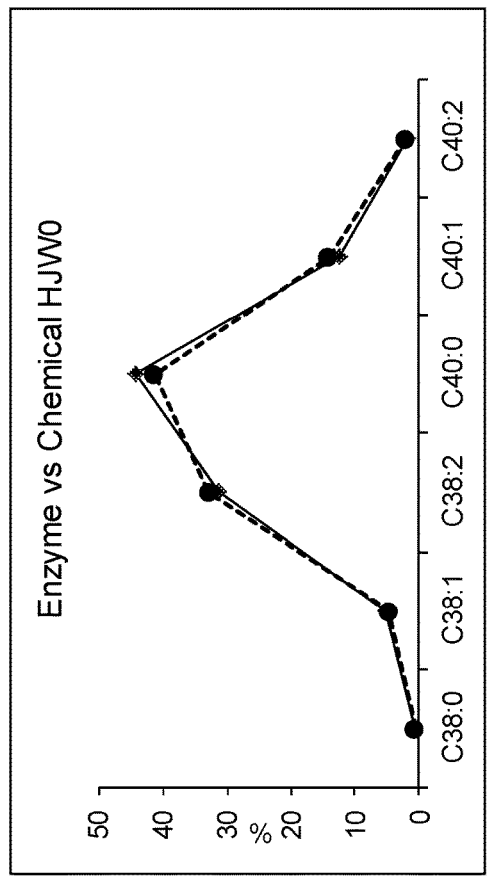
FIG. 4 is a comparison chart showing the distribution of jojoba wax ester carbon lengths in a transesterified product stream from a jojoba wax ester feedstock for a chemically catalyzed process and an enzyme catalyzed process.
Figure 5:
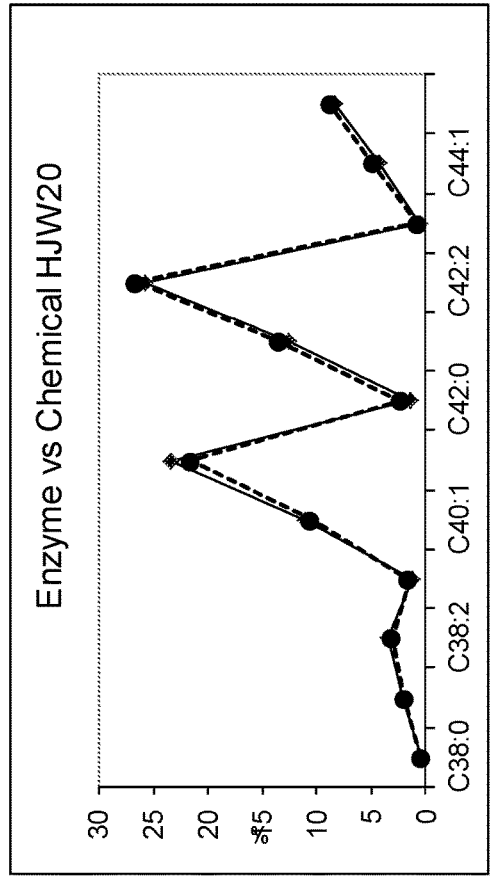
FIG. 5 is a comparison chart showing the distribution of jojoba wax ester carbon lengths in a transesterified product stream from a jojoba wax ester combined with about 20% by weight of hydrogenated jojoba wax ester feedstock for a chemically catalyzed process and an enzyme catalyzed process.
Figure 6:
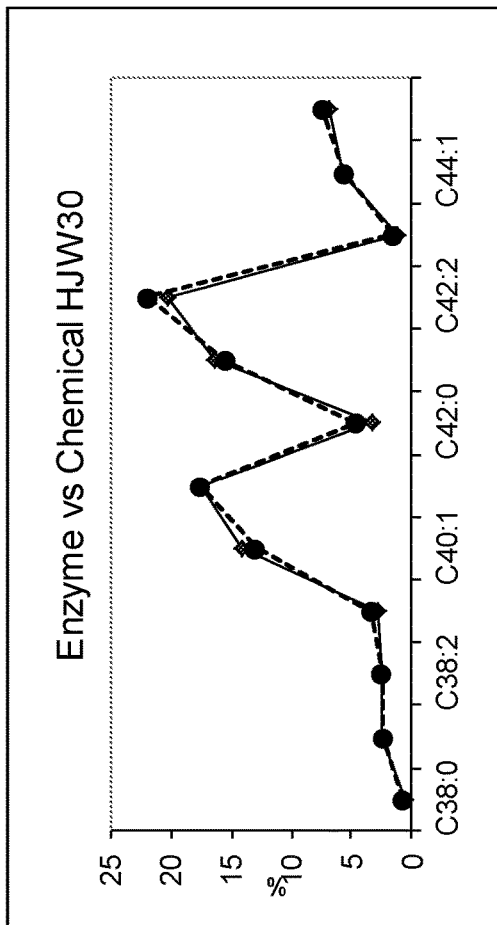
FIG. 6 is a comparison chart showing the distribution of jojoba wax ester carbon lengths in a transesterified product stream from a jojoba wax ester combined with about 30% by weight of hydrogenated jojoba wax ester feedstock for a chemically catalyzed process and an enzyme catalyzed process.
Figure 7:
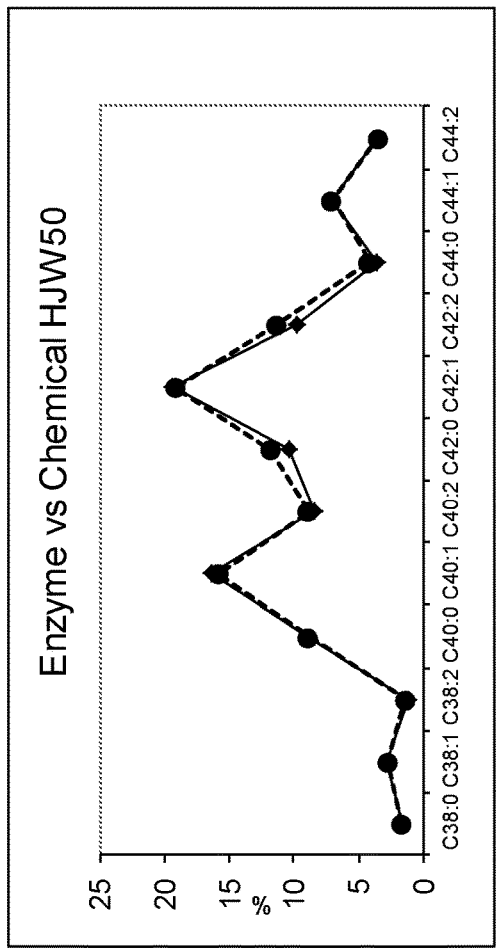
FIG. 7 is a comparison chart showing the distribution of jojoba wax ester carbon lengths in a transesterified product stream from a jojoba wax ester combined with about 50% by weight of hydrogenated jojoba wax ester feedstock for a chemically catalyzed process and an enzyme catalyzed process.

Referring to FIGS. 4-7, various comparison graphs of wax ester distributions for chemically catalyzed transesterified and enzyme catalyzed transesterified jojoba wax esters are illustrated. FIG. 4 is for a pure jojoba oil product (HJW0). The solid line shows the wax ester distribution for the chemically catalyzed process and the dotted line shows the wax ester distribution for the enzymatically catalyzed process. By observation, it is clear that the enzymatically catalyzed process successfully randomizes the various esters very similarly to the chemically catalyzed process. FIGS. 5, 6, and 7 show the wax ester distributions for transesterification products that have 20%, 30%, and 50% by weight hydrogenated jojoba wax esters added in, respectively. The similarity between the solid lines (chemical) and dotted (enzyme) demonstrate how the conversion rates of the enzymatic catalyzed process track those of the chemical catalyzed process. The differences between the two processes may contribute in part to the differences in functional performance and physical properties of the enzymatically catalyzed processed material from the chemically catalyzed material.

Lipases like those disclosed herein are conventionally used for processing triglycerides, and some have been specifically selected for processing triglycerides in particular ways. For example, some lipases are known as 1, 3 specific as they are capable of scissioning the alkyl esters in the 1 and 3 positions in a triglyceride while not affecting the alkyl ester at the 2 position. Such a lipase interacts with the triglyceride molecule on the exterior of the lipase surface. Other lipases operate when the alkyl ester is inserted into the lipase molecule itself. Obviously, 1, 3 lipases will differ in their ability to process various triglyceride molecules based on the structure of the alkyl esters and the triglyceride molecule due to various factors, including steric hindrance and other steric effects.

Interestingly, both 1, 3 lipases and lipases that operate using insertion of a triglyceride work equally well when used in jojoba ester transesterification reactions. This result is unexpected, as these lipases sterically interact quite differently with the molecules they are involved in catalyzing. Without being bound by any theory, it is possible that because a jojoba ester is primarily a long carbon chain without much molecular bending due to the ester group, both 1, 3 lipases and lipases that operate using insertion are able to interact sterically with the jojoba esters in ways that produce substantially the same catalytic effect. In other words, the long chain jojoba ester can fit into the opening in an insertion lipase and also slide into the active areas of a 1, 3 lipase. As this processing characteristic for lipase catalytic processing of jojoba wax esters is not a predictable result, this illustrates a unique aspect of processing jojoba wax esters using lipases.

Furthermore, conventional processing of triglycerides using lipases typically yields up to 4000 kg of product per kg of catalyst before the catalyst must be replaced. A wide variety of factors are attributed to the eventual denaturing of the catalyst, including gumming and contamination of the catalyst with water in the triglyceride feedstock. An example of a conventional transesterification process of a triglyceride vegetable oil feedstock may be found in U.S. Patent Application Publication No. 20130149414 to Favre et al., entitled "Processing of Vegetable Oils," filed Jun. 28, 2011, and published Jun. 13, 2013, the disclosure of which is incorporated entirely herein by reference. Testing using continuous flow reactors containing immobilized lipases on substrates demonstrated 96 days of 100% conversion using 0.46 kg of catalyst in each column. At the conclusion of this time period at which the catalyst needed to be replaced, 2305.15 kg of product was produced, which resulted in a kg of product to kg of catalyst ratio of 5011. This ratio of kg of product to kg of immobilized catalyst is over 20% greater than the ratio when the same lipase is used for triglyceride production. This result when the lipase is used for catalytic transesterification of jojoba oil significantly exceeds the conventional expectations for the lipase, and is an unexpected result that is not predicted by the results of conventional enzymatic triglyceride processing. In various implementations, the yield of an enzymatically transesterified wax ester reaction may yield least 4001 kg product/kg immobilized catalyst, at least 4100 kg product/kg immobilized catalyst, at least 4200 kg product/kg immobilized catalyst, at least 4300 kg product/kg immobilized catalyst, at least 4500 kg product/kg immobilized catalyst, at least 4700 kg product/kg immobilized catalyst, at least 48000 kg product/kg of immobilized catalyst, at least 4900 kg product/kg of immobilized catalyst, or even at least 5000 kg product/kg of immobilized catalyst.

In places where the description above refers to particular implementations of enzymatic catalytic transesterification systems, processes, and implementing components, sub-components, methods and sub-methods, it should be readily apparent that a number of modifications may be made without departing from the spirit thereof and that these implementations, implementing components, sub-components, methods and sub-methods may be applied to other enzymatic catalytic transesterification systems and processes.

What is claimed is:

1. A process for preparing enzymatically transesterified wax esters, the process comprising:
contacting a feedstock with a lipase enzyme catalyst, wherein the feedstock comprises jojoba wax esters, hydrogenated jojoba wax esters, and feedstock tocopherol; and
reacting the jojoba wax esters and the hydrogenated jojoba wax esters in the feedstock using the lipase enzyme catalyst to yield a product comprising the enzymatically transesterified wax esters and the feedstock tocopherol, wherein the reacting does not produce a free fatty alcohol.

2. The process of claim 1, wherein the jojoba wax esters comprise 20%-50% by weight of the hydrogenated jojoba wax esters.

3. The process of claim 2, wherein the jojoba wax esters comprise 20% by weight of the hydrogenated jojoba wax esters.

4. The process of claim 2, wherein the feedstock consists essentially of the jojoba wax esters, the hydrogenated jojoba wax esters, and the feedstock tocopherol.

5. The process of claim 4, wherein the feedstock comprises tocopherol naturally present in the feedstock.

6. The process of claim 5, wherein the feedstock further comprises added tocopherol.

7. The process of claim 1, wherein the product does not contain a free fatty alcohol.

8. The process of claim 2, wherein the product does not contain a free fatty alcohol.

9. The process of claim 1, wherein the lipase enzyme catalyst comprises a 1,3 selective lipase or a lipase that operates using insertion.

10. The process of claim 2, wherein the lipase enzyme catalyst comprises a 1,3 selective lipase or a lipase that operates using insertion.

11. The process of claim 4, wherein the lipase enzyme catalyst comprises a 1,3 selective lipase or a lipase that operates using insertion.

12. The process of claim 1, wherein the reacting step is continuous.

13. The process of claim 2, wherein the reacting step is continuous.

14. The process of claim 4, wherein the reacting step is continuous.

* * * * *

UNITED STATES PATENT AND TRADEMARK OFFICE
CERTIFICATE OF CORRECTION

PATENT NO. : 12,281,350 B2
APPLICATION NO. : 18/159735
DATED : April 22, 2025
INVENTOR(S) : Jeff Addy et al.

Page 1 of 1

It is certified that error appears in the above-identified patent and that said Letters Patent is hereby corrected as shown below:

In the Specification

In Column 3, Line 54 delete "a" and insert -- an --, therefor.
In Column 13, Line 9 delete "j of oba" and insert -- jojoba --, therefor.
In Column 13, Line 18 delete "Transeesterified" and insert -- Transesterified --, therefor.

Signed and Sealed this
Fifteenth Day of July, 2025

Coke Morgan Stewart
*Acting Director of the United States Patent and Trademark Office*